US010675381B2

(12) United States Patent
Fernandez et al.

(10) Patent No.: US 10,675,381 B2
(45) Date of Patent: Jun. 9, 2020

(54) DECELLULARIZED BIOMATERIAL AND METHOD FOR FORMATION

(71) Applicant: Clemson University, Clemson, SC (US)

(72) Inventors: Christopher Fernandez, Clifton, NJ (US); Jeremy Mercuri, Piedmont, SC (US)

(73) Assignee: Clemson University Research Foundation, Clemson, SC (US)

( * ) Notice: Subject to any disclaimer, the term of this patent is extended or adjusted under 35 U.S.C. 154(b) by 0 days.

(21) Appl. No.: 15/758,511

(22) PCT Filed: Sep. 8, 2016

(86) PCT No.: PCT/US2016/050689
§ 371 (c)(1),
(2) Date: Mar. 8, 2018

(87) PCT Pub. No.: WO2017/044570
PCT Pub. Date: Mar. 16, 2017

(65) Prior Publication Data
US 2018/0256784 A1 Sep. 13, 2018

Related U.S. Application Data

(60) Provisional application No. 62/215,475, filed on Sep. 8, 2015.

(51) Int. Cl.
*A61L 27/36* (2006.01)
*A61F 2/44* (2006.01)
*A61L 27/38* (2006.01)
*C12N 5/00* (2006.01)

(52) U.S. Cl.
CPC .......... *A61L 27/3687* (2013.01); *A61F 2/442* (2013.01); *A61L 27/3612* (2013.01); *A61L 27/3658* (2013.01); *A61L 27/3683* (2013.01); *A61L 27/3691* (2013.01); *A61L 27/3834* (2013.01); *A61L 27/3856* (2013.01); *C12N 5/0018* (2013.01); *A61L 2430/06* (2013.01); *A61L 2430/38* (2013.01); *C12N 2533/90* (2013.01); *C12N 2537/00* (2013.01)

(58) Field of Classification Search
CPC ............ A61L 27/3856; A61L 27/3683; A61L 27/3658; A61L 2430/38; A61F 2/44; C12N 2533/90
See application file for complete search history.

(56) References Cited

U.S. PATENT DOCUMENTS

| 6,723,335 | B1 | 4/2004 | Moehlenbruck et al. |
| 6,969,404 | B2 | 11/2005 | Ferree |
| 7,157,428 | B2 | 1/2007 | Kusanagi et al. |
| 7,195,912 | B2 | 3/2007 | Takezawa et al. |
| 7,217,294 | B2 | 5/2007 | Kusanagi et al. |
| 7,220,281 | B2 | 5/2007 | Lambrecht et al. |
| 8,137,688 | B2 | 3/2012 | Zahos et al. |
| 8,652,209 | B2 | 2/2014 | Tornier et al. |
| 8,936,642 | B2 | 1/2015 | Ferree |
| 8,945,223 | B2 | 2/2015 | Trieu |
| 9,005,289 | B1 | 4/2015 | Mercuri et al. |
| 9,011,543 | B2 | 4/2015 | Trieu et al. |
| 9,039,769 | B2 | 5/2015 | O'Halloran et al. |
| 2002/0198599 | A1 | 12/2002 | Haldimann |
| 2004/0059418 | A1 | 3/2004 | McKay et al. |
| 2007/0003525 | A1 | 1/2007 | Moehlenbruck et al. |
| 2007/0093905 | A1 | 4/2007 | O'Neil et al. |
| 2007/0233259 | A1 | 10/2007 | Muhanna et al. |
| 2008/0014179 | A1 | 1/2008 | Ferree |
| 2008/0021563 | A1 | 1/2008 | Chudzik |
| 2008/0065218 | A1 | 3/2008 | O'Neil |
| 2016/0243282 | A1 | 8/2016 | Simionescu et al. |

FOREIGN PATENT DOCUMENTS

| EP | 1614402 | 1/2006 |
| WO | WO 2004/069296 | 8/2004 |
| WO | WO 2006/095342 | 9/2006 |
| WO | WO 2008/078157 | 7/2008 |

OTHER PUBLICATIONS

Mercuri et al., Journal of Biomedical Materials Research A, 2011, vol. 96, Issue 2, p. 422-435.*
Wikipedia "Normalization", retrieved on Sep. 6, 2019, 3 pages of PDF.*
Adams, M. "Biomechanics of Back Pain." *Acupuncture in Medicine* 22(4), (2004), 178-88.
Antoniou et al. "The human lumbar intervertebral disc: Evidence for changes in the biosynthesis and denaturation of the extracellular matrix with growth, maturation, ageing, and degeneration," *J Clin Invest.* 221, (1996), 1153-161.
Atlas, et al. "Long-Term Outcomes of Surgical and Nonsurgical Management of Lumbar Spinal Stenosis: 8 to 10 Year Results from the Maine Lumbar Spine Study," *Spine* 30(8), (2005), 936-943.
Balagué, et al. "Non-specific low back pain." *Lancet* 379, (2012), 482-491.
Boden, et al. "Abnormal Magnetic-Resonance Scans of the Cervical Spine in Asymptomatic Subjects, A Prospective Investigation." *The Journal of Bone and Joint Surgery.* American vol. 72(8). (1990), 1178-84, (Abstract only).

(Continued)

*Primary Examiner* — Kade Ariani
(74) *Attorney, Agent, or Firm* — Dority & Manning, P.A.

(57) ABSTRACT

Methods for developing a decellularized tissue and biomaterials for use as biomimetic grafts or in vitro cellular scaffolds formed with the decellularized tissue are described. The biomaterials are particularly well suited for use as an intervertebral disc graft. The decellularized tissue is formed from an intervertebral disc source tissue and can be substantially decellularized and substantially free of potential immunogenic material (e.g., DNA and RNA), while maintaining ECM materials including both glycosaminoglycan and collagen.

10 Claims, 11 Drawing Sheets

(56) References Cited

OTHER PUBLICATIONS

Braga-Vilela, et al. 2008. "Extracellular Matrix of Porcine Pericardium: Biochemistry and Collagen Architecture." *Journal of Membrane Biology* 221(1), (2008), 15-25.

Bron, et al. "Repair, Regenerative and Supportive Therapies of the Annulus Fibrosus: Achievements and Challenges." *European Spine Journal* 18(3), (2009), 301-13.

Carragee, et al. "Clinical Outcomes after Lumbar Discectomy for Sciatica: The Effects of Fragment Type and Anular Competence." *The Journal of Bone and Joint Surgery.* American 85-A(1), (2003), 102-8.

Chan, et al. "Decellularized bovine intervertebral disc as a natural scaffold for xenogenic cell studies." *Acta Biomater.* 9, (2013), 5262-72.

Cloyd, et al. "Material properties in unconfined compression of human nucleus pulposus, injectable hyaluronic acid-based hydrogels and tissue engineering scaffolds." *Eur. Spine J.* 16, (2007), 1892-1898.

Crapo, et al. "An Overview of Tissue and Whole Organ Decellularization Processes." *Biomaterials* 32(12), (2011), 3233-43.

Atlas, R. "In Project Briefs: Back Pain Patient Outcomes Assessment Team (BOAT)." *Agency for Healthcare Research and Quality.* (1994).

Freeman, et al. "Compressive properties of fibrous repair tissue compared to nucleus and annulus." *J. Biomech.* 46, (2013), 1714-1721.

Freytes, et al. "Analytically Derived Material Properties of Multilaminated Extracellular Matrix Devices Using the Ball-Burst Test." *Biomaterials* 26(27), (2005), 5518-31.

Gilbert, et al., 2009. "Quantification of DNA in Biologic Scaffold Materials." *The Journal of Surgical Research* 152(1), (2009), 135-39.

Green, et al. "Tensile Properties of the Annulus Fibrosus II. Ultimate Tensile Strength and Fatigue Life." *European Spine Journal* 2, (1993), 209-14. (Abstract only).

Guterl, et al. "Challenges and Strategies in the Repair of Ruptured Annulus Fibrosus." *European Cells & Materials* 25, (2013), 1-21.

Holzapfel et al., "Single lamellar mechanics of the human lumbar anulus fibrosus," *Biomech. Model Mechanobiol.* 3(3), (2005), 125-140.

Hu, et al. "A Population-Based Study of Reoperations After Back Surgery," *Spine* 22(19), (1997), 2265-2270.

Hughes, et al. "The Pathogenesis of Degeneration of the Intervertebral Disc and Emerging Therapies in the Management of Back Pain." *The Journal of Bone and Joint Surgery.* British vol. 94(10), (2012), 1298-1304.

Jensen, et al. "Magnetic Resonance Imaging of the Lumbar Spine in People without Back Pain," *N Engl J Med* 331, (1994), 69-73.

Lequin, et al. "Primary Limited Lumbar Discectomy with an Annulus Closure Device: One-Year Clinical and Radiographic Results from a Prospective, Multi-Center Study," *Korean Spine* 9(4), (2012), 340-347.

Long, et al. "Mechanical Restoration and Failure Analyses of a Hydrogel and Scaffold Composite Strategy for Annulus Fibrosus Repair." *Acta Biomaterialia* 30, (2015), 116-25.

Martin, et al. "Expenditures and health status among adults with back and neck problems." *JAMA* 299, (2008), 656-664.

Mercuri, et al. "Regenerative potential of decellularized porcine nucleus pulposus hydrogel scaffolds: stem cell differentiation, matrix remodeling, and biocompatibility studies." *Tissue Eng. Part A* 19, (2013), 952-66.

Mercuri, et al. "Novel tissue-derived biomimetic, scaffold for regenerating the human nucleus pulposus" *J. Biomed. Mater. Res.—Part A* 96 A, (2011), 422-435.

Mwale, et al. "Distinction between the extracellular matrix of the nucleus pulposus and hyaline cartilage: a requisite for tissue engineering of intervertebral disc." *Eur Cell Mater* 8, (2004), 58-64.

Nerurkar, et al. "Nanofibrous Biologic Laminates Replicate the Form and Function of the Annulus Fibrosus." *Nature Materials* 8(12), (2009), 986-92.

O'Connell, et al. "Human Annulus Fibrosus Material Properties from Biaxial Testing and Constitutive Modeling are Altered with Degeneration." *Biomechanics and Modeling in Mechanobiology* 11(3-4), (2012), 493-503.

Rémi, et al. "Pericardial Processing: Challenges, Outcomes and Future Prospects." *Biomaterials Science and Engineering*, (2011), 437-57.

Schoenfeld, et al. "Treatment of Lumbar Disc Herniation: Evidence-Based Practice." *International Journal of General Medicine* (3), (2010), 209-14.

Tedder, et al. "Stabilized Collagen Scaffolds for Heart Valve Tissue Engineering," *Tissue Engineering. Part A* 15(6), (2009), 1257-68.

Urban, et al. "Degeneration of the Intervertebral Disc." *Arthritis Res Ther* 5(3), (2003), 120.

Urban, et al. "The Nucleus of the Intervertebral Dtsc from Development to Degeneration." *American Zoologist* 40(1), (2000), 53-61.

Vallfors, B. "Acute, Subacute and Chronic Low Back Pain: Clinical Symptoms, Absenteeism and Working Environment." *Scan J Rehab Med Suppl* 11, (1985), 1-98. (Abstract only).

Wilke, et al. "New in Vivo Measurements of Pressures in the Intervertebral Disc in Daily Life." *Spine* 24(8), (1999), 755-62.

PCT International Search Report & Written Opinion, PCT/US16/50689, (dated 2017).

Yaun, et al. "Effects of nucleus pulposus cell-derived acellular matrix on the differentiation of mesenchymal stem cells" *Biomaterials* 34 (2013) pp. 3948-3961.

Partial European Search Report (Appl. No. 16845015.3) dated Apr. 12, 2019.

\* cited by examiner

| NO. | SONICATION TREATMENT NO. | 70% EtOH TREATMENT TIME | DECELLURIZATION SOLUTION | | | | | NUCLEASE SOLUTION | | TREATED TISSUE | |
|---|---|---|---|---|---|---|---|---|---|---|---|
| | | | EDTA (w/v%) | TRITON X-100 (v/v%) | DEOXYCHOLIC ACID (w/v%) | SODIUM AZIDE (w/v%) | SDS (w/v%) | DNase (mU/mL) | RNase (mU/mL) | DNA (ng/mg) GAG (mg/mg) AVERAGE | HISTOLOGY |
| 1 | 6 | - | 0.2 | 0.64 | 1 | 0.02 | - | 720 | 720 | DNA = 7.19 GAG = 52.63 | NUCLEI VISIBLE ECM FADED BLUE |
| 2 | 12 | - | 0.2 | 0.6 | 1 | 0.02 | - | 720 | 720 | DNA = 15.26 GAG = 59.81 | " |
| 3 | 6 | - | 0.2 | 0.6 | 1 | 0.02 | - | 720 | 720 | DNA = 10.21 GAG = 70.67 | " |
| 4 | 12 | - | 0.2 | 0.6 | 1 | 0.02 | - | 720 | 720 | DNA = 7.53 GAG = 53.04 | NUCLEI VISIBLE ECM DEEP BLUE |
| 5 | 6 | - | 0.2 | 0.6 | 1 | 0.02 | - | 720 | 720 | DNA = 11.59 GAG = 83.09 | " |
| 6 | 3 | - | 0.2 | 0.6 | 1 | 0.02 | - | 720 | 720 | DNA = 10.45 GAG = 57.99 | " |
| 7 | 3 | - | 0.4 | 1.2 | 2 | 0.04 | - | 720 | 720 | DNA = 33.61 GAG = 216.98 | EMPTY LACUNAE FADED BLUE ECM |
| 8 | 3 | 30 min | 0.2 | 0.6 | 1 | 0.02 | - | 720 | 720 | DNA = 15.59 GAG = 103.42 | " |
| 9 | 3 | 60 min | 0.2 | 0.6 | 1 | 0.02 | - | 720 | 720 | DNA = 9.07 GAG = 184.53 | " |
| 10 | 3 | 45 min | 0.2 | 0.6 | 1 | 0.02 | - | 720 | 720 | DNA = 33.08 GAG = 208.93 | NUCLEI PRESENT FADED BLUE ECM |
| 11 | 3 | - | 0.2 | 0.6 | - | 0.02 | - | 720 | 720 | DNA = 15.22 GAG = 133.59 | NUCLEI PRESENT INTENSE BLUE ECM |
| 12 | 3 | - | 2.21 mM | - | - | - | 0.4 | 720 | 720 | DNA = 23.31 GAG = 71.92 | NUCLEI PRESENT FADED BLUE ECM |
| 13 | 3 | - | 0.4 | 1.2 | - | 0.02 | - | 720 | 720 | DNA = 9.07 GAG = 205.5 | EMPTY LACUNAE DEEP BLUE ECM |

FIG. 2

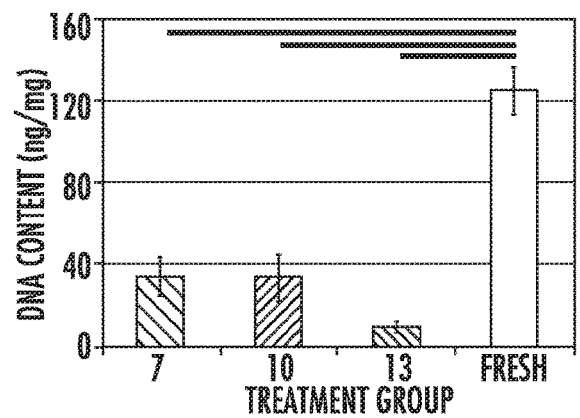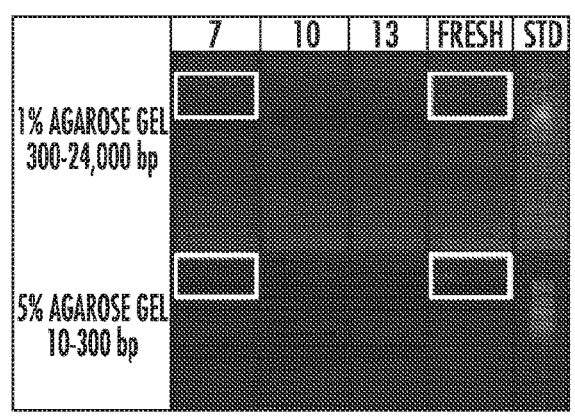
FIG. 3A
FIG. 3B
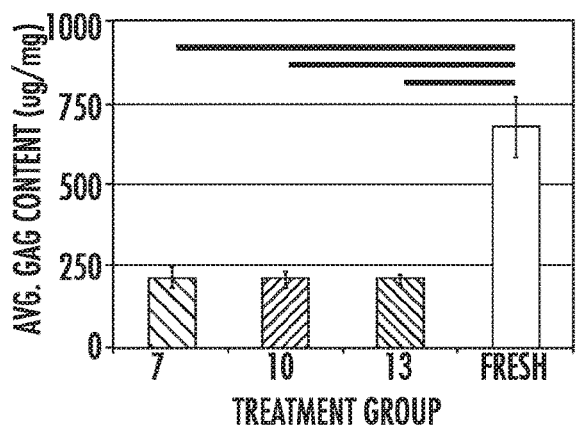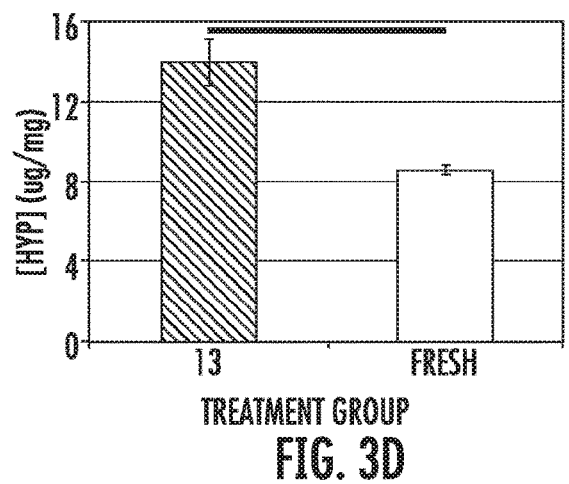
FIG. 3C
FIG. 3D

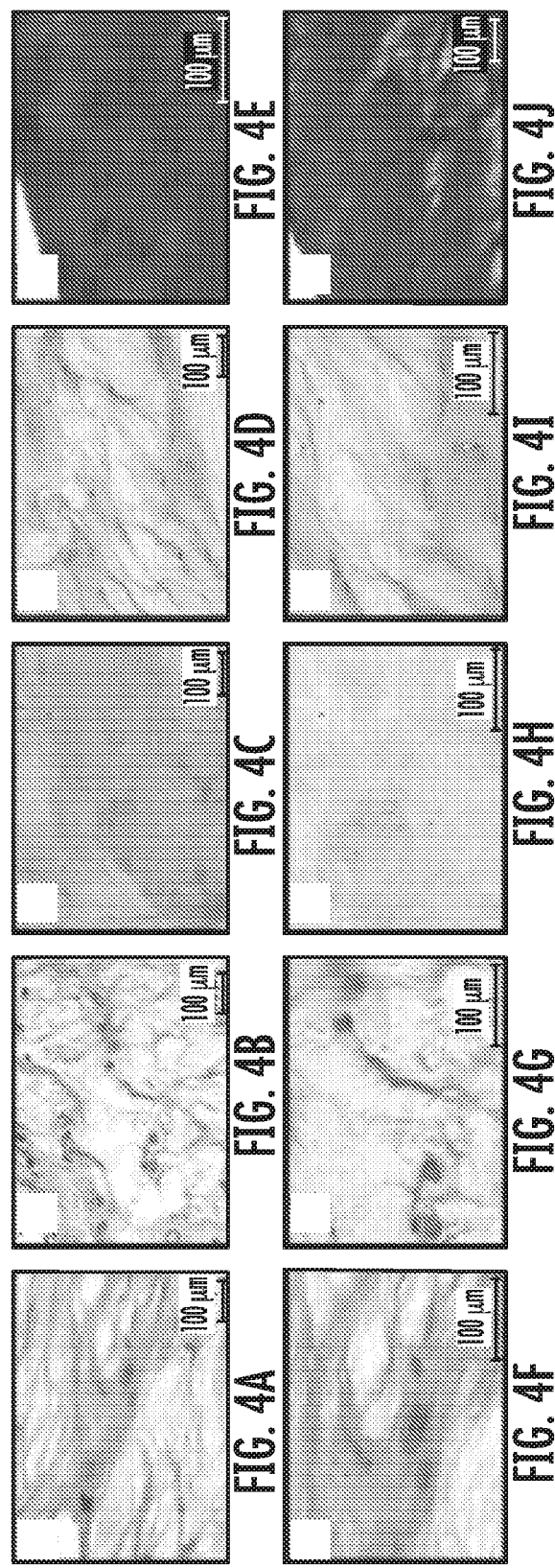

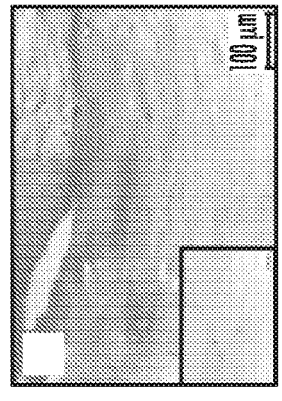 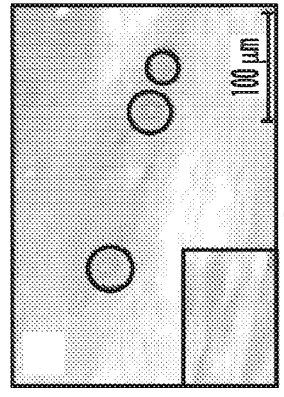 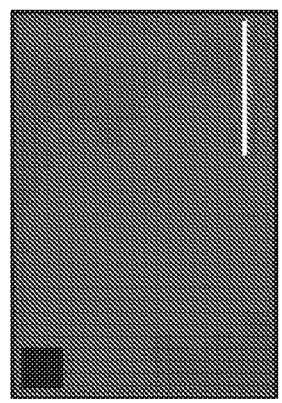 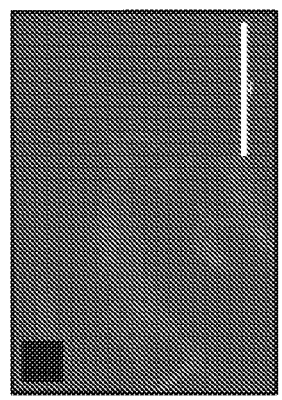
FIG. 5A    FIG. 5B    FIG. 5C    FIG. 5D
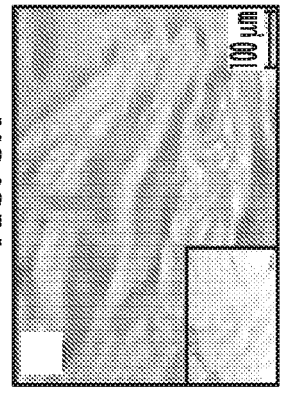 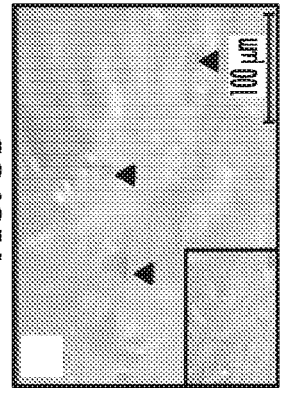 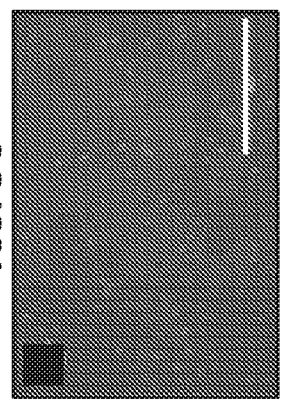 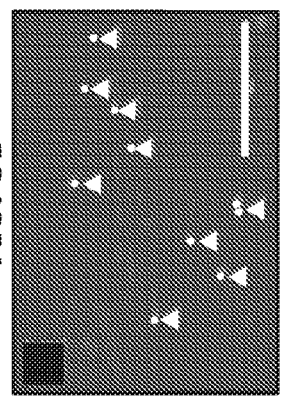
FIG. 5E    FIG. 5F    FIG. 5G    FIG. 5H

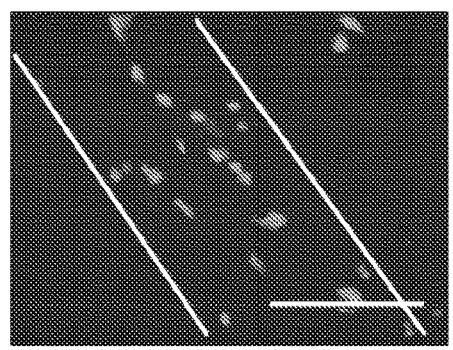
DAY 3 FIG. 10A
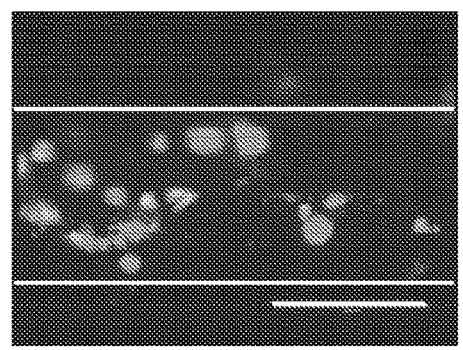
DAY 3 FIG. 10B
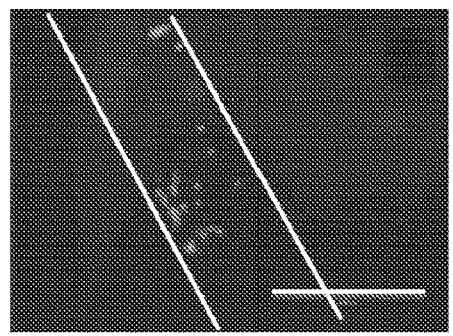
DAY 14 FIG. 10C
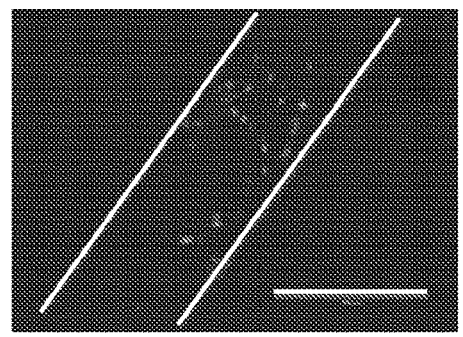
DAY 14 FIG. 10D
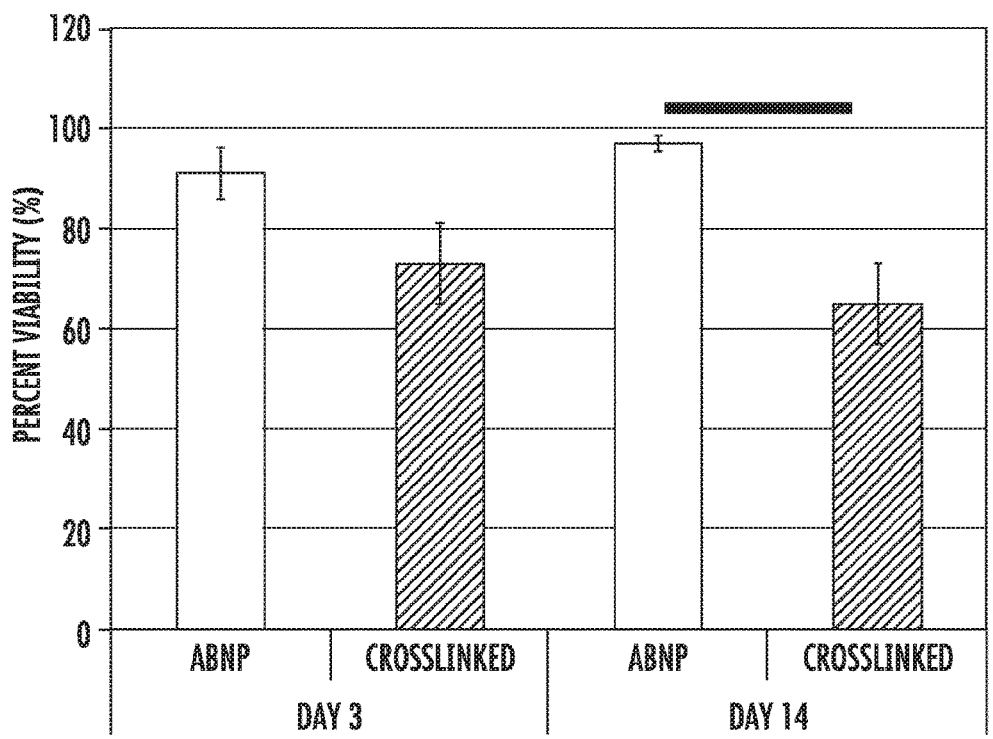
FIG. 10E

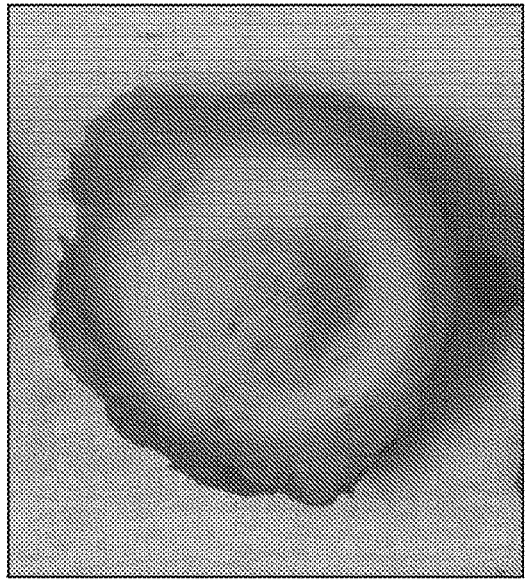
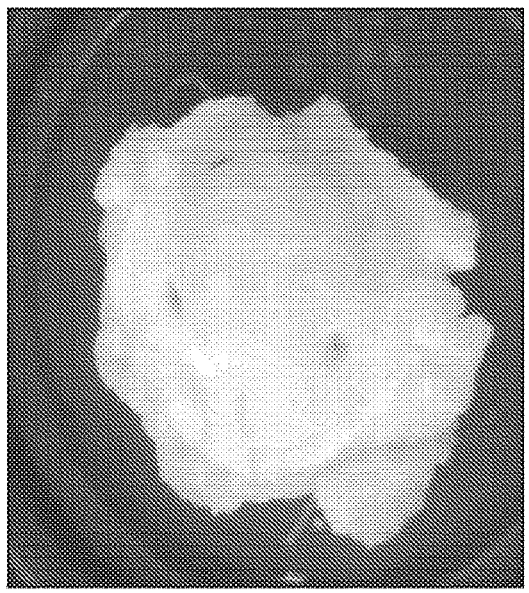
FIG. 11
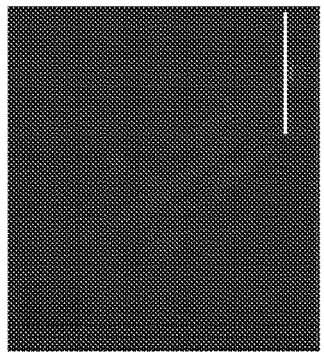
FIG. 12D
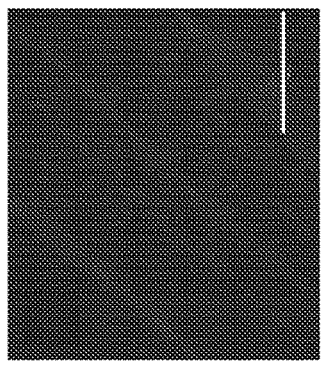
FIG. 12C
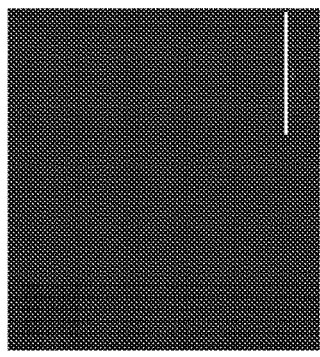
FIG. 12B
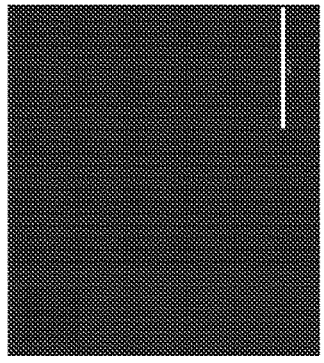
FIG. 12A

DECELLULARIZED BIOMATERIAL AND METHOD FOR FORMATION

CROSS REFERENCE TO RELATED APPLICATION

This application claims filing benefit of U.S. Provisional Patent Application Ser. No. 62/215,475 having a filing date of Sep. 8, 2015, which is incorporated herein by reference in its entirety.

BACKGROUND

Low back pain poses a significant socioeconomic burden with a lifetime prevalence of 84% and estimated U.S. expenditures of $85.9 billion per year. Although the cause of low back pain is difficult to pinpoint; it often originates from degenerating or herniated intervertebral discs. As shown in FIG. 1, an intervertebral disc 12 includes the nucleus pulposus 10 surrounded by the annulus fibrosus 16. A disc 12 forms a cushion between adjacent vertebrae 14 that allows for flexibility and motion and supports compressive loads during activities of daily living. The nucleus pulposus is a highly hydrated tissue composed primarily of type II collagen and the proteoglycan aggrecan. Intervertebral disc degeneration is a multifactorial process that manifests initially as biochemical degradation of the nucleus pulposus 10. Intervertebral disc herniation is commonly the result of an increase in intradiscal pressure due to abrupt loading that exceeds the strength of the restraining annulus fibrosus 16 of the disc 12 leading to extrusion of nucleus pulposus tissue 10 from the disc 12. Both pathologies can result in decreased disc height and irritation of adjacent nerve roots leading to the generation of back and leg pain as well as limb weakness.

Current therapies for both intervertebral disc degeneration and herniation are palliative and merely delay invasive surgical management in the form of discectomy, spinal fusion and total disc replacement. While these procedures may temporarily relieve pain, they do not attempt to replace, restore or regenerate healthy nucleus pulposus tissue. Additionally, there are concerns with the use of surgical methodologies that may promote re-herniation, altered spinal biomechanics, and accelerated degeneration in adjacent discs.

Regenerative medicine approaches to intervertebral disc degeneration repair have been investigated both in vitro and in vivo. For instance, injection of growth factors and stem cells into the nucleus pulposus have been examined, but have demonstrated limited success due short half-life, leakage, and inability to maintain an appropriate phenotype due to the altered tissue extracellular matrix (ECM) microarchitecture.

Tissue engineering strategies combining a supporting scaffold and an alternative healthy cell source (i.e. stem cells) together provide a promising avenue for developing viable nucleus pulposus tissue constructs. However, success of such approaches relies largely upon the development of a biomaterial scaffold that mimics the biochemistry and mechanical properties of the subject and that can function to deliver, protect, and provide instructive cues to stem cells such that they attain the appropriate phenotype and produce nucleus pulposus-specific ECM. Examples of biomaterial scaffolds investigated include pre-formed and injectable hydrogels composed of type II collagen-hyaluronic acid and cross-linked alginate.

An alternative scaffold formation method includes the decellularization of a source tissue. Decellularization attempts to remove host cells from the source tissue while maintaining intact, tissue-specific ECM. One primary advantage of this approach is that the remaining ECM provides cues that can advantageously affect migration, proliferation, differentiation and subsequent tissue-specific ECM production by seeded cells. Successful decellularization has proven difficult however, as it requires complete removal of potential immunogenic materials while maintaining suitable levels of desirable ECM components such that function of the scaffold can be maintained. Attempts have been made to form suitable implantable graft materials from xenograft or allograft sources. While some approaches have demonstrated the ability to retain key ECM components in physiologically relevant quantities and ratios, these methods unfortunately left the source cells devitalized but sequestered within the tissue. Others have demonstrated successful removal of cell DNA via disruption of the native ECM, but the resulting scaffold material also showed significant reduction in GAG, which would significantly affect function of the resulting graft material.

What is needed in the art is a biomaterial scaffold that can recapitulate native nucleus pulposus microarchitecture, biochemistry, and mechanical properties, and that can support cells seeded thereon as a route to aiding patients with intervertebral disc degeneration and intervertebral disc herniation.

SUMMARY

According to one embodiment, disclosed is a biomaterial that includes a decellularized intervertebral disc tissue. The decellularized intervertebral disc tissue can be an allograft or xenograft intervertebral disc tissue that has been treated so as to be substantially free of cell nuclei. In addition, the decellularized intervertebral disc tissue can include nucleus pulposus tissue that has a glycosaminoglycan content of about 200 micrograms (µg) or greater per milligram (mg) dry weight of the decellularized nucleus pulposus tissue and can include nucleic acids in an amount of about 50 nanograms (ng) or less per mg dry weight of the decellularized nucleus pulposus tissue. In one embodiment, the decellularized intervertebral disc tissue can include both nucleus pulposus tissue and annulus fibrosus tissue. In another embodiment, the decellularized intervertebral disc tissue can include nucleus pulposus tissue and can be substantially free of annulus fibrosus tissue. In another embodiment, the decellularized intervertebral tissue can include annulus fibrosus tissue and can be substantially free of nucleus pulposus tissue.

Also disclosed is a method for forming a biomaterial. The method can include subjecting a source intervertebral disc tissue, e.g., an allograft or xenograft nucleus pulposus tissue, annulus fibrosus tissue, or an entire intervertebral disc to both chemical and mechanical treatments. For instance, a chemical treatment can include contacting the intervertebral disc tissue with a decellularization solution that includes one or more non-ionic surfactants and a protease inhibitor, optionally in conjunction with additional materials (e.g., antimicrobials, ionic surfactants, etc.). The decellularization solution can be agitated while the intervertebral disc tissue is held in contact with the solution. In addition, the decellularization solution containing the intervertebral disc tissue can be subjected to ultrasonication. Following, the intervertebral disc tissue can be contacted with an enzyme solution, for instance to remove remaining DNA and RNA.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which:

FIG. 2 is a table (Table 1) showing details of 13 different decellularization solutions and processes.

FIG. 3 compares the DNA content of fresh bovine nucleus pulposus to tissue decellularized as disclosed herein both quantitatively (panel A) and qualitatively (panel B). Glycosaminoglycan (GAG) content of decellularized and fresh tissues are compared at panel C. Hydroxyproline (HYP) content of decellularized and fresh tissues are shown at panel D. Horizontal bars connecting groups indicate significant differences ($p<0.05$).

FIG. 4 illustrates several different decellularized tissues (panels A-D and F-I) and fresh, untreated tissue (panels E and J) following alcian blue counterstained with nuclear fast depicting GAG and cell nuclei (panels A-E 200× magnification, F-J 400× magnification).

FIG. 5 presents histological analysis of treated tissues (panels A-D) compared to fresh untreated tissue (panels E-H).

FIG. 10, upper panel, presents representative live/dead images of noncrosslinked (panels A and C) and EDC/NHS treated (panels B and D) treated tissue after 3 days (panels A and B; 200× total magnification) and 14 days (panels C and D; 100× total magnification), respectively. Panel E presents a graphical representation of hAMSC viability within non-crosslinked ("ABNP") and EDC/NHS treated ("crosslinked") tissue after 3 and 14 days in culture. Horizontal bars connecting groups indicate statistical differences ($p<0.05$).

FIG. 11 provides representative images of a fresh intact intervertebral disc (left) and a decellularized intact intervertebral disc (right).

FIG. 12 illustrates the results of ethidium staining for residual DNA for fresh nucleus pulposus (panel A) and fresh annulus fibrosus (panel C) compared to decellularized nucleus pulposus (panel B) and decellularized annulus fibrosus (panel D) of intervertebral discs demonstrating the absence of residual DNA following decellularization.

Figure 1:
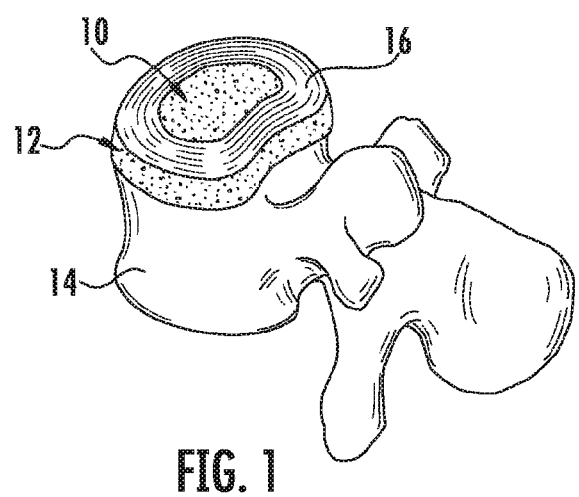
FIG. 1 illustrates a typical intervertebral disc and associated vertebrae.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

In general, the present disclosure is directed to methods for developing a decellularized biomaterial that can be utilized in one embodiment as an implantable graft material and can be particularly suited for use as a intervertebral graft material. In particular, the biomaterial can be substantially decellularized and can be substantially free of potential immunogenic material (e.g., DNA and RNA), while maintaining ECM materials including both glycosaminoglycan and collagen in an amount so as to provide excellent cell supporting and mechanical characteristics as an intervertebral graft.

As used herein, the term "substantially free" means that the presence of a particular component is either not detected using known assays, or if it is detected, it is only present in an amount that is in accordance with the tissue regulations of the U.S. Food and Drug Administration (FDA) as set forth in Title 21 Code of Federal Regulations (CFR), Parts 1270 and 1271, herein incorporated by reference. In various aspects, "substantially free" can include a tissue has been reduced in the amount of the component by about 90% or more, about 95% or more, about 98% or more, or about 99% or more as compared to the amount of the component by dry weight in natural, untreated tissue. In certain aspects, "substantially free" means that the tissue is completely free of the component.

As used herein "substantially decellularized" means that the tissue has been reduced in the amount of cells by about 70% or more, about 80% or more, about 90% or more, about 95% or more, about 98% or more, or about 99% or more as compared to the amount of cells by dry weight in natural, untreated tissue. In certain aspects, "substantially decellularized" means that the tissue is completely free of cells.

Disclosed methods can produce biomimetic biomaterials through decellularization of source xenogeneic or allogeneic intervertebral disc tissue according to a process that can remove host DNA as well as other potentially immunogenic materials while maintaining native ECM components. In particular, disclosed methods can retain physiologically relevant amounts of glycosaminoglycan (GAG) and collagens, e.g., type II collagen. As such, the mechanical characteristics of the biomaterials, e.g., unconfined static and dynamic compressive mechanical properties, can approach values reported for human intervertebral disc components (e.g., nucleus pulposus). Moreover, cellular scaffolds formed of the biomaterials can maintain viability of cells, e.g., stem cells that can be planted on the biomaterials. Accordingly, the biomaterials can be particularly well suited for use as regenerative intervertebral disc graft materials. However, it should be understood that the biomaterials are not limited to utilization as intervertebral disc graft materials and can be utilized in other applications including as other graft materials (e.g., articular cartilage graft materials, osteochondral graft materials, etc.) as well as for use in in vitro or ex vivo applications. For instance, the biomaterials can be particularly well suited for use as scaffolding materials for supporting growth and development of extrinsic cells, i.e., cells loaded onto the biomaterials following formation such as stem cells, ex vivo differentiated cells, etc., that can include intervertebral disc-derived cells or any other type of cell(s) for study purposes as well as for implantation/grafting purposes.

According to one embodiment, disclosed treatment methods can remove about 90% or more, e.g., about 93% or more, of the DNA of the source tissue, with no detectable residual base-pairs present. For instance, treated nucleus pulposus tissue can exhibit a total DNA content of about 50 ng or less DNA/mg dry tissue weight, or even lower in some embodiments, such as about 20 ng or less DNA/mg dry tissue weight, or about 10 ng or less DNA/mg dry tissue weight. Treated annulus fibrosus tissue can exhibit a total DNA content of about 70 ng or less DNA/mg dry tissue weight, or even lower in some embodiments, such as about 65 ng or less DNA/mg dry tissue weight or about 50 ng or less DNA/mg dry tissue weight. Moreover, treated tissues can have little or no DNA over about 200 base-pair fragment length, with a lack of visible nuclear material via DAPI or H&E staining and an absence of intact residual cell nuclei and of high and low molecular weight host DNA fragments.

Treatments can also retain glycosaminoglycan (GAG) of the source tissue. For instance treated nucleus pulposus tissue can retain GAG in an amount of about 200 µg or more of per milligram of nucleus pulposus tissue dry weight, or higher in other embodiments such as about 210 µg or more per mg dry weight, about 220 or more per mg dry weight, or about 250 µg per mg dry weight in some embodiments. When considering treatment of annulus fibrosus tissue, the tissue can retain GAG in an amount of about 100 µg or more per mg dry weight, about 115 or more per mg dry weight, or about 130 µg per mg dry weight in some embodiments. The retention of this key ECM component, along with collagens, and in particular collagen type II, is critical for the mechanical function of the intervertebral disc tissue, as it creates the osmotic properties and swelling pressures required to support compressive loads and prevent nerve and blood vessel in-growth into the intervertebral disc.

The biomaterials can retain significant amounts of GAG as well as collagen type II from the source tissue. For instance, treated tissue can retain a hydroxyproline (HYP) content (as measure of type II collagen content) such that the treated tissue has a GAG:HYP ratio of about 15:1 or higher, for instance from about 10:1 to about 25:1 in some embodiments. The biomaterials can retain significant levels of other collagens (e.g., collagen type IX, collagen type XI, etc.) that can improve the function of the biomaterials.

Without wishing to be bound to any particular theory, it is believed that the relatively high quantities of ECM materials retained in the biomaterials may support earlier tissue regeneration in grafting applications as less ECM would need to be produced by seeded cells in order to achieve proper mechanical function of the tissue. As such, the biomaterials can be ideally suited for use as intervertebral graft materials in lumbar as well as cervical applications, for instance as a surrogate to regenerate nucleus pulposus tissue and/or annulus fibrosus tissue that has succumbed to degeneration or extrusion in patients with intervertebral disc degeneration or intervertebral disc herniation.

The biomaterials can also exhibit viscoelastic properties that can mimic or re-establish the native properties of the host materials, e.g., the human nucleus pulposus and/or annulus fibrosus that it can augment or replace. For instance, the biomaterials can exhibit a storage modulus of about 6 kilopascals (kPa) or greater, for instance from about 6 kPa to about 15 kPa in some embodiments. A biomaterial can exhibit a loss modulus of about 1 kPa or greater, for instance from about 1.5 kPa to about 5 kPa in some embodiments. A biomaterial can exhibit a complex modulus of about 6 kPa or greater, for instance from about 6 kPa to about 15 kPa or greater, and can exhibit a phase angle of about 15° or greater, for instance from about 15° to about 27° in some embodiments.

The biomaterials can exhibit mechanical properties that approach healthy human intervertebral disc tissue values, even in the absence of cell seeding; suggesting that the biomaterials may can function mechanically immediately upon implantation. Moreover, the viscoelastic properties can improve upon cell seeding and development of additional ECM by the transplanted cells.

In general, the source tissue material for development of the decellularized biomaterial can be obtained from any xenogeneic or allogeneic source including, without limitation, porcine, bovine, human cadaver, etc. In one embodiment, the source tissue can be bovine intervertebral disc tissue, and in one particular embodiment, caudal (tail) intervertebral disc tissue. Bovine caudal source tissue may be beneficial in some embodiments due to the similarity in size (e.g., height to diameter ratio) to human lumbar intervertebral disc tissue as well as due to similarities in resting stress and biochemistry to native human intervertebral disc tissue.

The source tissue can be any portion or all of an intervertebral disc. For instance, in one embodiment, the source tissue can be essentially limited to nucleus pulposus tissue and absent of annulus fibrosus or other disc tissue. However, the disclosure is not limited to only nucleus pulposus source tissue. In other embodiments, a source tissue can include all or part of a nucleus pulposus in conjunction with other tissue of the source intervertebral disc, such as all or part of the adjoining annulus fibrosus. For instance, in one embodiment, an entire intervertebral disc including both the annulus fibrosus and the nucleus pulposus can be treated. Alternatively, the source tissue can be limited to annulus fibrosus tissue and all or a part of the annulus fibrosus can be decellularized, essentially absent of any nucleus pulposus or other disc tissue.

To form the biomaterial, the source tissue material (e.g., bovine caudal nucleus pulposus) can be treated according to a combination of chemical and mechanical treatments. The chemical treatment can include contacting the source tissue with a decellularization solution that includes at least one non-ionic surfactant, optionally in conjunction with one or more additional surfactants.

Optionally, prior to contact between the source tissue and the decellularization solution, the process can include an ethanol pre-wash, which can dehydrate the source tissue and encourage uptake of the components (and in particular the surfactant(s)) of the decellularization solution into the interstice of the tissue. For instance, the source tissue can be immersed in an ethanol solution (e.g., a 70% ethanol solution) for a period of time of about 15 minutes or more, for instance from about 30 minutes to about 60 minutes in some embodiments, optionally in conjunction with agitation of the mixture. Inclusion of an ethanol pre-wash may be particularly beneficial in those embodiments in which the decellularization solution includes fewer and/or lower concentrations of surfactants.

The decellularization solution can include at least one non-ionic surfactant. Examples of non-ionic surfactants can include, without limitation, an polyethylene oxide based surfactant or a polysorbate based surfactant such as Triton™ X-100 (t-octylphenoxypolyethoxyethanol), Tween® 20 (polysorbate 20), Tween® 80 (polysorbate 80), Igepal® CA630 (ethoxylated nonylphenol), etc. In general, the decellularization solution can include a non-ionic surfactant in an amount of about 0.5 v/v %, for instance from about 0.5 v/v % to about 2 v/v % in some embodiments. In one embodiment, the decellularization solution can include the non-ionic surfactant in a higher concentration than has been utilized in the past, particularly in those embodiments in which an ethanol pre-wash is not utilized, as discussed above. For instance, in some embodiments, the decellularization solution can include one or more non-ionic surfactants in an amount of about 1 v/v % or greater.

The decellularization solution can include additional surfactants in conjunction with one or more non-ionic surfactants. For example, a decellularization solution can include one or more anionic, zwitterionic, and/or cationic surfactants in addition to the non-ionic surfactant. Examples of anionic, zwitterionic, and cationic surfactants can include, without limitation, Triton™ X-200, sodium deoxycholate, CHAPS, sodium dodecyl sulfate (SDS), N-lauroyl-sarcosinate, Sulfobetain-10 and Sulfobetain-16. When included, an ionic surfactant can generally be present in the decellularization solution in an amount of from about 0.5 w/v % to about 2 w/v %. It should be understood, however, that the presence of ionic surfactants are not required in the decellularization solution. In fact, it has been surprisingly found that certain ionic surfactants, such as SDS, that have been considered to be necessary in the past for successful decellularization, are not necessary in the disclosed decellularization solutions and can be omitted.

In addition to the surfactant(s), the decellularization solution can include one or more protease inhibitors. Protease inhibitors can be included in the solution to prevent degradation of the extracellular matrix. Collagen-based connective tissues such as nucleus pulposus contain proteases and collagenases as endogenous enzymes in the extracellular protein matrix. Additionally, certain cell types that may be present in the source tissue including smooth muscle cells, fibroblasts and endothelial cells contain a number of these enzymes inside the lysosomes. When these cells are damaged during the decellularization process, the lysosomes are ruptured and their contents released. As a result, the extracellular matrix can undergo severe damage from protein, proteoglycan and collagen breakdown. As such, the decellularization solution can include one or more protease inhibitors. Suitable protease inhibitors can include, without limitation, N-ethylmaleimide (NEM), phenylmethylsulfonylfluoride (PMSF), ethylenediamine tetraacetic acid (EDTA), ethylene glycol-bis-(2-aminoethyl(ether)NNN'N'-tetraacetic acid, ammonium chloride, elevated pH, apoprotinin and leupeptin. In general, the decellularization solution can include a protease inhibitor in an amount of from about 0.1 w/v % to about 1 w/v %, for instance, from about 0.2 w/v % to about 0.6 w/v %.

The decellularization solution can include additional components as are generally known in the art including, without limitation, one or more salts (e.g., KCl, NaCl), one or more organic or inorganic buffers, one or more antibiotics/antimycotics (e.g., penicillin, vancomycin, streptomycin, gentamycin, kanamycin, neomycin, sodium azide ($NaN_3$)) with or without anti-fungal agents (e.g., Amphotericin B, Nystain)), etc.

The tissue can be held in the decellularization solution with agitation, so as to encourage contact between the tissue and the solution components. Periodically, e.g., every 12-24 hours, the solution can be changed out for fresh solution.

In conjunction with contact (e.g., immersion) of the tissue with the decellularization solution, the solution can be periodically subjected to ultrasonication for a period of time, generally from about 5 minutes to about 60 minutes, for instance from about 10 minutes to about 30 minutes in some embodiments. The ultrasonication can generally be at a power level of about 10 W or greater, for instance about 50 W or greater, or about 100 W or greater, for instance from about 10 W to about 1000 W in some embodiments.

The frequency of the ultrasonication can generally be about 20 kHz or greater, for instance about 50 kHz or greater, or about 100 kHz or greater in some embodiments, such as from about 20 kHz to about 200 kHz. By way of example, a suitable ultrasonication condition may be from about 50 W to about 100 W at about 20 kHz to about 50 kHz for about 10 minutes.

The ultrasonication can be carried out periodically over the course of a treatment regimen. For instance, ultrasonication can be carried out once every 12-24 hours. In one embodiment, the ultrasonication can be carried out after contacting the tissue with fresh decellularization solution. For instance, following any pretreatment, a nucleus pulposus source tissue can be immersed in a decellularization solution and subjected to a sonication treatment. Following a period of ultrasonication, the tissue can be agitated in the decellularization solution for a period of time (e.g., 12-24 hours). Following a contact period under agitation, the tissue can be placed in a fresh decellularization solution and the process can be repeated (ultrasonication followed by contact under agitation). The total treatment time can generally be from about 1 day to about 7 days, in order to obtain essentially complete decellularization, for instance, from about 2 days to about 5 days in some embodiments.

Following this portion of the decellularization treatment, the tissue can be contacted with an enzyme solution to produce an enzyme-treated biomaterial. A nuclease enzyme can generally be used to breakdown any remaining nucleic and ribonucleic acids. Enzymes can include nucleases such as endonucleases (e.g., DNAse, RNAse, Benzonase). An enzyme treatment can generally be carried out according to standard procedures as are known in the art.

Additional treatments can be optionally carried out to modify the physical characteristics of the biomaterials. For example, in one embodiment, biomaterial can be cross-linked with collagen and/or elastin cross-linking agents. Cross-linking can be utilized to affect multiple characteristics of a biomaterial. For example, the level of cross-linking can influence the porosity and various strength characteristics of the biomaterial. Cross-linking of the biomaterial can also be utilized to control the degradation characteristics of the material following implantation. Degradation of collagen is a naturally occurring phenomenon prevalent in intervertebral disc pathology. Collagen is rapidly broken down by collagenases, e.g., matrix metalloproteinases (MMPs), produced in the area. Accordingly, crosslinking of a biomaterial can be of benefit to slow the natural degradation processes of the material particularly when considering the biomaterials for use as a nucleus pulposus graft material.

Any suitable crosslinking agent can be utilized. For example, collagen fixatives such a glutaraldehyde, carbodiimide, polyepoxides, etc. and/or elastin fixatives including polyphenolic compounds (tannic acid, pentagalloyl glucose, etc.) and the like can be utilized to cross-link the structural proteins of the multi-layer construct.

The decellularization procedure can effectively and efficiently be applied to intervertebral disc source tissue to provide a mechanically competent biomimetic biomaterial capable of supporting stem cell viability. Beneficially, the biomaterials may be used in one embodiment in conjunction with stem cells for regenerative medicine approaches in treatment of intervertebral disc degeneration and intervertebral disc herniation in order to mitigate progressive dysfunction of the intervertebral disc.

The present disclosure may be better understood with reference to the Examples set forth below.

Example 1

Tissue Harvest

Bovine tails were harvested from 2-3 years old cows at a local abattoir and were transported on wet ice to the lab. Betadine® was applied to the exterior of the tail to remove bacteria. Excess fascia and muscle were removed from the tails with a scalpel; the location of intervertebral discs was visually confirmed prior to excision immediately adjacent to the endplates via bone cutters. An 8 mm biopsy punch was used to remove nucleus pulposus tissue from the center of the intervertebral disc. Fresh nucleus pulposus samples were stored at −20° C. and served as controls for experiments. Samples for decellularization were immediately placed either in ethanol or various decellularization solutions.

Decellularization Methods

Thirteen different decellularization treatment methods were examined as summarized in the table presented in FIG. 2. The methods differed by chemical decellularization solution, number of ultrasonication (40 kHz) treatments, total treatment duration, and inclusion of ethanol pre-treatment. All decellularization solutions (except sample no. 12) were made in 50 mM Tris buffer (pH 7.5) containing 2% antibiotic/antimycotic. 10 tissue samples (10 samples/100 mL of each solution) were placed in their respective solutions and ultrasonicated for 10 minutes prior to undergoing constant agitation (150 RPM) on an orbital shaker at room temperature. Every twenty-four hours thereafter decellularization solutions were changed for fresh solution and samples were ultrasonicated for an additional 10 minutes. This process was repeated for a total of either three or six days. At the completion of the process, all samples were rinsed in sequential changes of distilled water, 70% ethanol and distilled water again; each for 30 minutes under orbital agitation (150 RPM) at room temperature prior to undergoing nuclease treatment at 37° C. for 48 hours. All nuclease solutions were made in 1×PBS (pH 7.5) containing 5 mM magnesium chloride. Following nuclease treatment all samples were thoroughly rinsed in distilled water for one hour under agitation.

Decellularization Efficacy Screening

The efficacy of each treatment method was initially screened via quantitative biochemical assays used to measure residual bovine DNA and glycosaminoglycan (GAG) content via PicoGreen™ (Thermo Fisher Scientific) and DMMB assays, respectively. Additionally, histological analyses were performed on OCT embedded cryosections to detect the presence of residual bovine cell nuclei via Alcian blue counterstained with nuclear fast red. Acceptance criteria were established a priori to indicate successful decellularization and included: 1) an average residual DNA content of less than or equal to 50 ng DNA/mg dry tissue, 2) an average residual GAG content of greater than or equal to 200 μg GAG/mg dry tissue and 3) no histological evidence of intact cell nuclei within the decelled NP tissue. All samples that met the acceptance criteria were further evaluated for residual DNA via agarose gel electrophoresis.

DMMB Analysis for GAG

Fresh (n=6) and treated tissue samples (n=6/treatment) were frozen for 24 hours at −80° C. prior to lyophilization. Sample dry weights were recorded for data normalization prior to complete digestion in PBE buffer containing papain (5 mM L-cysteine, 100 mM dibasic phosphate buffer, 5 mM EDTA, 12.50 μg/mL papain, pH 7.5) for 24 hours at 65° C. Fresh and treated samples were diluted by 1000× and 100λ, respectively in PBE buffer prior to combining 50 μL of each sample with 200 μL of DMMB reagent (40 mM NaCl, 40 mM Glycine, 46 μM DMMB, pH 3.0) in a 96-well plate. Absorbance was read at 525 nm and GAG content was determined from a standard curve developed from known concentrations of chondroitin-6-sulfate.

PicoGreen® Analysis for dsDNA

Total double stranded DNA content of fresh (n=6) and treated tissue samples (n=6/decell treatment) were quantified using a PicoGreen® assay according to manufacturer's instructions. Briefly, papain digested samples were thawed and diluted 2× in a 1×TE buffer prior to combining 100 μL of sample with 100 μL of PicoGreen® reagent in a black-walled 96-well plate. Fluorescence was detected using excitation and emission wavelengths of 480 nm and 520 nm, respectively. DNA content was determined from a standard curve developed from known concentrations of lambda DNA supplied by the assay manufacturer.

Agarose Gel Electrophoresis

DNA was purified from aliquots of papain digested samples of both fresh (n=3) and treated tissue samples (n=3/treatment) using a Qiagen DNeasy® Blood & Tissue extraction kit according to manufacturer's instructions. A total of 30 μl of purified DNA sample was loaded into each well of an agarose gel containing ethidium bromide. Two concentrations of agarose gels were used in order to detect high and low molecular weight ranges of residual DNA. A wide range DNA ladder (300-24,000 bp, exACTGene 24 kb) was ran on a 1% agarose gel at 100V for 60 minutes. A low range DNA ladder (10-300 bp, O'GeneRuler Low Range DNA) was run on a 5% agarose gel at 75V for 60 minutes. Gels were imaged in a bio-imager (Bio-Rad) using an ethidium bromide filter to detect the presence of DNA bands. All samples were run against a DNA standard.

Decellularization treatment no. 13 was selected as an example treatment protocol that provided a treated tissue devoid of intact cell nuclei and residual DNA while maintaining an average GAG content of ≥200 μg/mg dry sample. This treated biomaterial scaffold material is hereafter referred to as the acellular bovine nucleus pulposus (ABNP) scaffold, and was further characterized as follows:

Water Content Analysis of ABNP Scaffold

Percent water content was determined by the following equation: $[(W_{wet}-W_{dry})/W_{wet}]\times 100$, where $W_{wet}$ was sample wet weights and $W_{dry}$ was the sample dry weight determined following lyophilization.

Hydroxyproline Analysis of ABNP Scaffold

Collagen content of fresh bovine NP (n=3) and ABNP scaffolds (n=6) were quantified using a hydroxyproline (HYP) assay according to the manufacturer's instructions (Sigma—MAK008). Hydrolyzed samples from both fresh and ABNP scaffolds were diluted 100× in 12M HCl and 10 µL of each sample were analyzed at 550 nm. HYP content was calculated using a standard curve developed from serial dilutions of a known concentration of HYP. HYP Values were normalized to sample dry weight.

Histology and Immunohistochemistry (IHC) of ABNP Scaffold

Samples of fresh bovine NP and ABNP scaffolds were fixed in 10% neutral buffered formalin for 24 hours. Fixed samples were then washed in 1×PBS with 0.01% sodium azide for 30 minutes and then soaked in a 15% sucrose solution at 4° C. overnight. Subsequently, samples were placed in a 30% sucrose solution for 2 hours at 4° C., and then placed in a 50:50 30% sucrose and OCT solution for 2 hours at room temperature. Finally, samples were placed in OCT for 2 hours then transferred to OCT molds for cryosectioning at −20° C. until solid. Cryosections of 8 µm thickness were collected on positively charged slides and stored at −20° C. until staining. All imaging was performed using a Zeiss AxioVert.A1 inverted microscope with Axiovision software.

Immunohistochemistry for Type II Collagen

Frozen sections of fresh bovine NP (n=3) and ABNP scaffolds (n=3) were fixed for 20 minutes in cold acetone. Slides were rinsed twice in TBS for 5 minutes, permeabilized in 0.025% Triton X-100, non-specific binding and endogenous peroxidases were blocked with normal serum and a solution of 0.3% hydrogen peroxide in 0.3% normal serum, respectively. A rabbit polyclonal antibody towards bovine type II collagen (Abcam—ab78482; 1:50 dilution) was incubated overnight at 4° C. prior to thorough rinsing and incubation at room temperature for 30 minutes with a secondary biotinylated antibody and avidin biotin complex according to manufacturer's instructions (Vectastain® ABC Elite Kit Rabbit IgG—Vector Labs). A DAB substrate kit (Vector Labs: SK4100) was used to visualize positive staining according to manufacturer's instructions prior to counterstaining with a dilute hematoxylin solution for 30 seconds. To account for non-specific binding of the secondary antibody; select samples did not receive primary antibody. Additional positive and negative controls for type II collagen staining included chondrogenically induced hAMSC cell pellets and decellularized porcine pericardium, respectively (data not shown).

Alcian Blue and Nuclear Fast Red Histology Staining

Frozen sections of fresh bovine NP (n=6) and ABNP scaffolds (n=6) were rinsed in tap water prior to being placed in 3% acetic acid for 1 minute followed by a 1% alcian blue in 3% acetic acid (pH 2.5) solution for 3 minutes. Slides were rinsed in tap water for 1 minute and counterstained in 0.1% nuclear fast red for 2 minutes.

DAPI Nuclear Staining

Frozen slides of fresh bovine NP (n=3) and ABNP scaffolds (n=3) were rinsed in 1×PBS for 1 minute and placed in a 300 mM DAPI solution for 5 minutes in the dark. Slides were washed in PBS and then immediately transported for imaging under a fluorescent microscope fitted with a 460 nm filter.

Ethidium Bromide DNA Staining

Samples of fresh bovine NP (n=3) and ABNP scaffolds (n=3) were placed in a solution of 2 mM ethidium bromide in PBS for 30 minutes. Tissues were then thinly sectioned using a scalpel blade and imaged under a fluorescent microscope.

Sample Preparation and Testing Conditions

Fresh and ABNP samples were frozen at −20° C., embedded in OCT and sectioned to a thickness of approximately 6 mm for all mechanical testing. Prior to removing samples from OCT, a 6 mm diameter biopsy punch was used to ensure consistent sample diameters which resulted in a 1:1 diameter to height ratio. Subsequently, all samples (both fresh and ABNP) were allowed to thaw and free swell in the testing tank (which contained a solution of 1×PBS and 1% protease inhibitor) for at least one hour at room temperature (25° C.). All samples were tested while submerged in a solution of 1×PBS and protease inhibitor using a Bose Electrofoce® 3200 series mechanical test frame equipped with a 1000 g load cell fitted with a testing tank according to standard practice.

Unconfined Compression

Unconfined compressive stress relaxation experiments were performed on fresh (n=5) and ABNP scaffolds (n=5) to determine the compressive properties of the specimens once equilibrium relaxation was attained. Briefly, a compression platen was brought in contact with a stationary testing platform and the displacement measurement was zeroed prior to pre-loading. Pre-loading consisted of compressing the specimens in displacement control until a 0.05N compressive load was achieved (which resulted in approximately 12% total strain). Platen displacement was held constant for 20 minutes allowing for the sample to equilibrate. Sample heights were determined at the end of pre-loading based on the initial zeroed displacement by the test software. Subsequently, stress relaxation testing was conducted which consisted of subjecting the preconditioned samples to a final strain of 16% (based on sample heights determined after preconditioning) using 4% strain increments (starting at 8%) held for 20 minutes each until the change in load was less than 0.025N/minute. Data was collected in WinTest 7 using level crossing with each change of 0.025N being recorded. NIH Image J software was used to measure and confirm sample height and diameter at the applied peak strain and at equilibrium. Intrinsic equilibrium Young's modulus of the solid matrix was determined through the equilibrium response during stress relaxation at 8%, 12%, and 16% applied strains by dividing the equilibrium stress by the respective applied strain. Percent relaxation was determined at each applied strain using the following equation: $[(\sigma_p-\sigma_e)/\sigma_p]\times 100$, where $\sigma_p$=peak stress and $\sigma_e$=equilibrium stress. Poisson's ratio (u), shear modulus (µ), and aggregate modulus ($H_A$) were determined assuming isotropic, homogeneous biphasic theory for cartilaginous materials as previously reported. Briefly, Poisson's ratio was measured directly from unconfined compression testing using an optical method. Briefly, direct lateral images of specimens were obtained at equilibrium following compression to 8 and 12% strain, respectively. Images of each specimen were obtained using a digital camera and a stationary metric calibrator located inside the testing tank. NIH Image J software was used in conjunction with the metric calibrator in order to determine equilibrium lateral expansion of the specimen immediately adjacent to the lower testing platform. Shear and aggregate moduli were determined through their relationships with both intrinsic equilibrium Young's modulus and Poisson's ratio via the following equations, respectively:

$$\mu = \frac{E}{2(1+\upsilon)}$$

$$H_A = \frac{E(1-\upsilon)}{(1+\upsilon)(1-2\upsilon)}$$

Unconfined Dynamic Mechanical Analysis (DMA)

DMA testing was used to determine the complex, storage, and loss modulus as well as phase angle of a second set of fresh bovine NP (n=6) and ABNP scaffolds (n=6). Similar to unconfined compression testing, samples were pre-loaded to 0.05N under displacement control and were then allowed to equilibrate for 20 minutes with the platen displacement being held constant. The height and width of each sample was confirmed from a direct lateral digital image taken at the end of the preconditioning period. Height data was input into the DMA testing software within WinTest 7. Samples were then preconditioned to 5% strain for 10 cycles prior to initiation of the test program, which was set to apply a cyclic strain of 8% (based on initial sample height) at a frequency of 0.01, 0.1, 1, and 10 Hz with a 20-minute relaxation between each test frequency.

ABNP Scaffold Cytotoxicity

Scaffolds were sterilized in 0.01% peracetic acid followed by washing three times for 15 minutes each in 1× sterile PBS. Scaffolds were then placed in a solution containing 50% FBS, 48% DMEM, and 2% AB/AM for 24 hours. Human amniotic mesenchymal stem cells (hAMSCs; passage 2) were obtained from consenting patients immediately following the delivery via elective cesarean section of full-term babies. Stem cells were isolated within 4 hours of delivery. Stem cells were seeded via drop-wise addition to the surface of the scaffolds at a density of 2,000 hAMSCs/mm$^2$. Seeded scaffolds were incubated at 37° C. for 3 hours to allow time for cells to attached prior to the addition of media (DMEM containing 10% FBS and 1% Ab/Am). Media was refreshed every 3 days. On days 3, 7, and 14 a live/dead assay was performed (n=3 per time point) was performed according to manufacturer's instructions (Biotium). ABNP scaffolds were sectioned using a scalpel blade and imaged under a fluorescent microscope. Three representative images of both live and dead staining were taken for each scaffold. Quantification of cells was performed by manually counting live and dead cells in each image. Percent viability was determined by dividing the number of live cells by the total number of cells.

ABNP Scaffold Crosslinking for Stem Cell Injection Studies

ABNP scaffolds were crosslinked in a solution of 30 mM 1-ethyl-3-(3-dimethylaminopropyl) carbodiimide HCL (EDC)/6 mM n-hydroxysuccinimide (NHS) in 50 mM beta-morpholinoethansulfonurea hydrate (MES) buffer (pH 5.5) for 30 minutes. Scaffolds were subsequently washed three times for 15 minutes each, sterilized in 0.1% peracetic acid, and washed again three times at 15 minutes each in 1× sterile PBS then were placed in a solution of 50% FBS, 48% DMEM, and 2% AB/AM for 24 hours prior to cell seeding/injection.

ABNP Scaffold Cell Injection

Injection of hAMSCs into ABNP scaffolds was investigated due to the observation that hAMSCs were not able to infiltrate the scaffold after 14 days of culture following seeding on the scaffold surface. Thus, a pilot study was initiated to determine if hAMSCs could be injected into the ABNP scaffolds. Preliminary studies were performed to confirm appropriate needle bore size for injection (i.e. what was the smallest bore needle diameter that could be used to inject stem cells without killing them due to shearing). A 28G needle was selected based on the results of the preliminary hAMSC viability studies after injection through various syringe needle diameters (data not shown). Scaffolds were injected with 150 μL of hAMSC suspension (4×10$^6$ cells/m L). Cell injected scaffolds were cultured for 3 and 14 days and cell viability was assessed using live/dead staining and fluorescent microscopy.

Statistical Analysis

Results are represented as a mean±standard error of the mean (SEM). For quantitative biochemical data obtained during decellularization screening studies, viability comparisons and mechanical data comparing across strain levels within each study group (ABNP vs Fresh); a one-way analysis of variance (ANOVA) using a Tukey's honest significant difference post hoc analysis for all pairwise comparisons was used. Mechanical data was also analyzed via a Students two-tailed t-test assuming equal variance in order to determine if differences between study groups (i.e. ABNP vs Fresh) existed within each applied strain (for stress relaxation testing) or test frequency (for DMA testing), respectively. Significance was defined in all cases as p<0.05.

Results

The effectiveness of decellularization procedures was initially screened by evaluating residual bovine DNA concomitant with the retention of GAG. Optimal decellularization procedures were defined as those that resulted in a tissue that contained less than 50 ng/mg DNA and maintained at least 200 μg/mg of GAG. Three decellularization procedures were identified based on these criteria: treatment nos. 7, 10, and 13, respectively (FIG. 2).

Evaluation of residual double stranded bovine DNA demonstrated significant reductions (p<0.01) in treatment nos. 7, 10, & 13 as compared to fresh tissue. These treatment groups contained 33.61±9.49 ng, 33.08±11.57 ng, and 9.07±1.95 ng DNA per mg sample dry weight, respectively (FIG. 3 at A). Interestingly, samples treated with SDS, a method commonly employed for tissue decellularization did not show statistical reductions in DNA content in treated tissue (71.31±30.59 ng DNA per mg dry weight). Compared to fresh bovine NP tissue (125.45±11.81 ng DNA per mg sample dry weight) there was a 73.2±7.56%, 73.63±9.22%, & 92.77±1.54% reduction in DNA content for nos. 7, 10, and 13, respectively.

No residual DNA fragments between 10-24,000 base pairs were detected in sample nos. 10 and 13, while residual fragments (indicated by light bands) appeared in the range of 300 bp for samples in treatment group 7 (FIG. 3 at B).

GAG quantification of decellularized tissue demonstrated the retention of 216.98±31.06 μg, 208.93±24.96 μg, and 205.5±16.00 μg GAG per mg sample dry weight using methods 7, 10, and 13 respectively (FIG. 3 at C). Expectedly, these values were statistically lower than values obtained for fresh tissue (677.66±93.22 μg GAG per mg sample dry weight) (FIG. 3 at C). Decellularization resulted in a reduction in average GAG content of 67.98±4.58%, 69.17±3.68%, & 69.68±2.36% in treatment nos. 7, 10, and 13 respectively. These findings were corroborated by Alcian blue staining (FIG. 4) which illustrated that the ECM in all decellularization samples was stained less intensely blue which indicated a reduction in GAG and a disrupted microarchitecture compared to fresh tissue sample. In FIG. 4, panels A and F illustrate sample no. 7, panels B and G illustrate sample no. 10, panels C and H illustrate sample no. 12, panels D and I illustrate sample no. 13 and panels E and J illustrate fresh, untreated tissue. The top panels in FIG. 4 are at 200× magnification and the lower panels are at 400× magnification. Further biochemical, histological and mechanical analysis was performed on samples subjected to decellularization method no. 13 and hereafter these samples were termed the "acellular bovine nucleus pulposus" (ABNP) scaffold.

ABNP scaffolds had significantly higher HYP content per dry mass when compared to fresh tissue ($p<0.05$) (FIG. 3 at D). More specifically, ABNP scaffolds contained nearly double the average amount of HYP as compared to fresh tissue (13.87±1.14 μg HYP/mg sample dry weight and 8.63±0.24 μg HYP/mg sample dry weight, respectively). Additionally, the GAG to HYP ratio was calculated to be approximately 15:1 for ABNP sample whereas fresh bovine NP tissue had an apparent ratio of 79:1.

IHC for collagen type II confirmed the presence of this ECM protein within both ABNP scaffolds and fresh tissue. Histological images (FIG. 5) illustrated intense brown (positive) staining in both the ABNP tissues (top panels A-D) and the fresh untreated tissue (panels E-H) throughout the ECM and pericellular regions as compared to negative controls. Immunohistochemistry for collagen type II is shown at panels A and E. Alcian blue counterstained with nuclear fast red depicting GAG and cell nuclei is shown at panels B and F. Black circles in panels B and F indicate empty lacunae; black arrowheads in fresh tissue images indicate cell nuclei. Ethidium bromide staining is shown at C and G indicating a lack of DNA fragments in the treated as compared to fresh tissue. DAPI staining is shown at D and H indicating a lack of nuclei in treated as compared to fresh tissue (arrow heads point to intact cell nuclei).

Figure 6A:
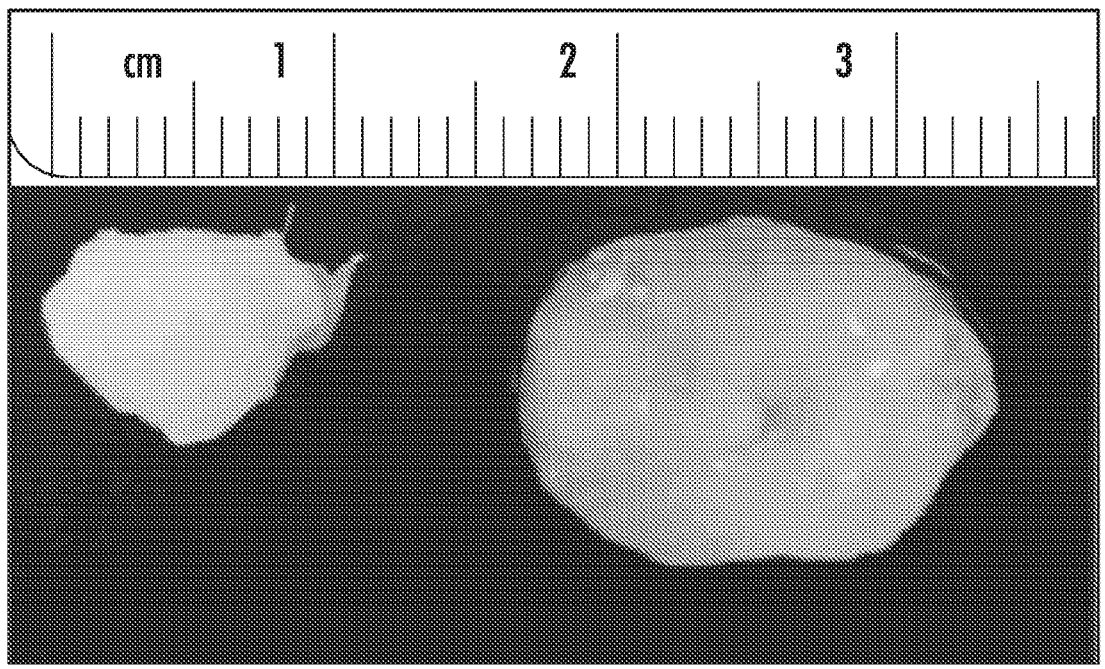
FIG. 6 presents a macroscopic image of fresh bovine nucleus pulposus (left) and treated tissue (right) (panel A). Representative unconfined compression stress relaxation curves are shown for fresh bovine tissue at panel B and for treated tissue at panel C showing relaxation profiles following the sequential application of 8, 12, and 16% strain, respectively.
Figure 6B:
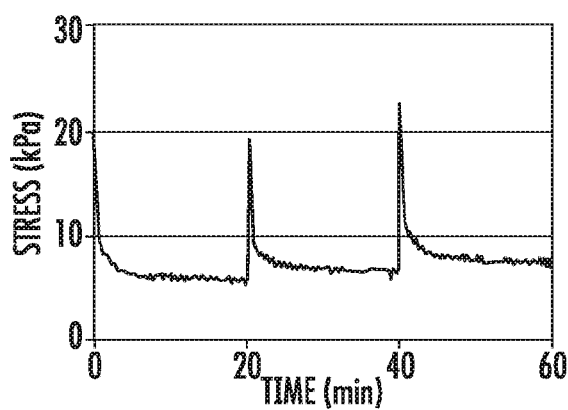
Figure 6C:
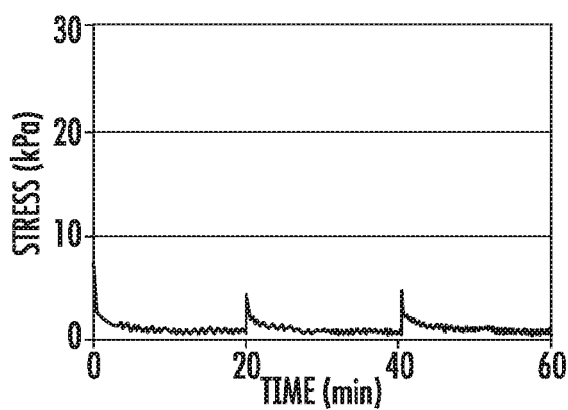

As can be seen in FIG. 6 (top panel), macroscopically both fresh tissue (left) and the ABNP scaffolds (right) maintained their firm shape. Fresh tissue and ABNP exhibited an average water content of 76.58±1.47% and 94.56±0.37%, respectively. Qualitative histology of the fresh tissue depicted the presence of cells in clusters/islands. The fresh tissue also stained more intensely with alcian blue (indicating the presence of GAG within the ECM) as illustrated by a deeper blue staining as compared to ABNP scaffolds (panels B and F, FIG. 5), which corroborated DMMB results. Additionally, empty lacunae were visible throughout the ECM of the ABNP scaffolds and ethidium bromide staining confirmed the absence of nucleic acids in ABNP samples (FIG. 5, panel D). However, nuclear material was present in the fresh tissue as indicated by positive DAPI staining (FIG. 5 panel H).

Figure 7A:
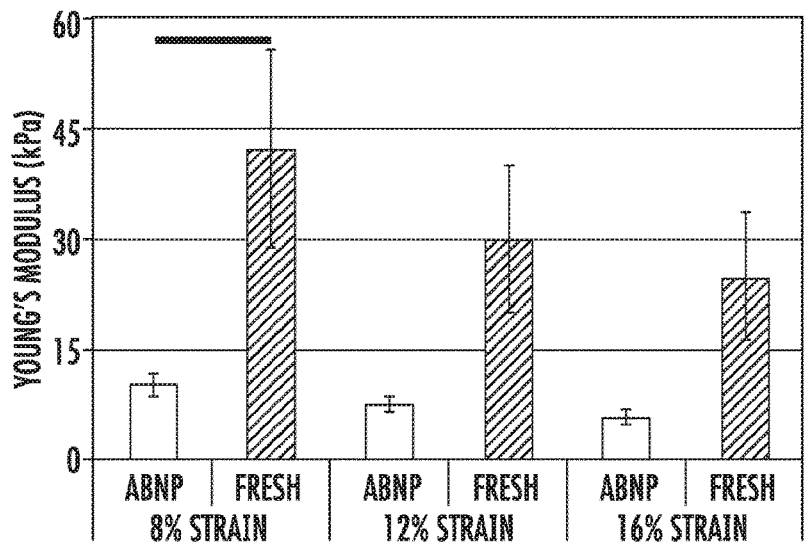
FIG. 7 presents equilibrium mechanical properties determined following stress relaxation testing to defined applied strain end-points for treated and fresh tissue including intrinsic Young's modulus (panel A), aggregate modulus (panel B), and shear modulus (panel C).
Figure 7B:
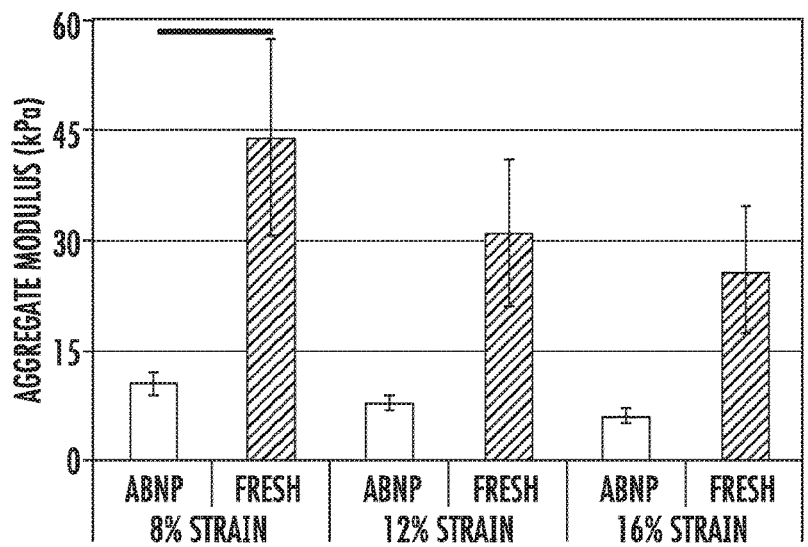
Figure 7C:
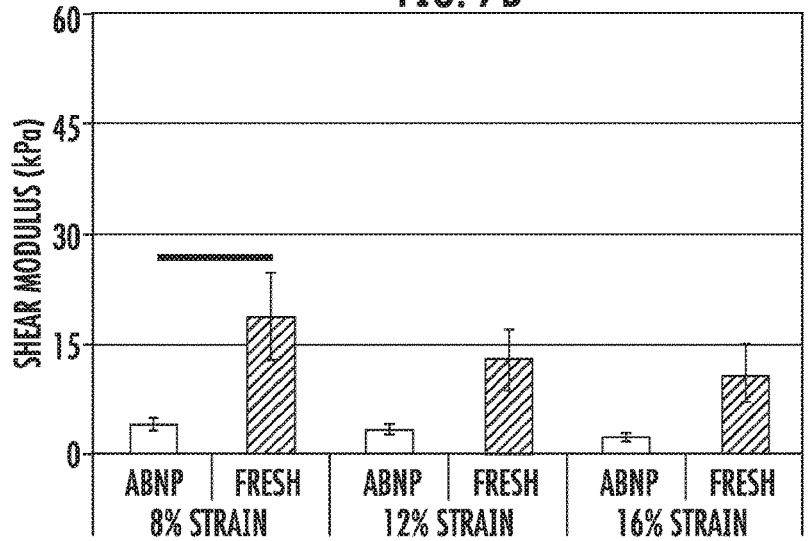
Figure 8A:
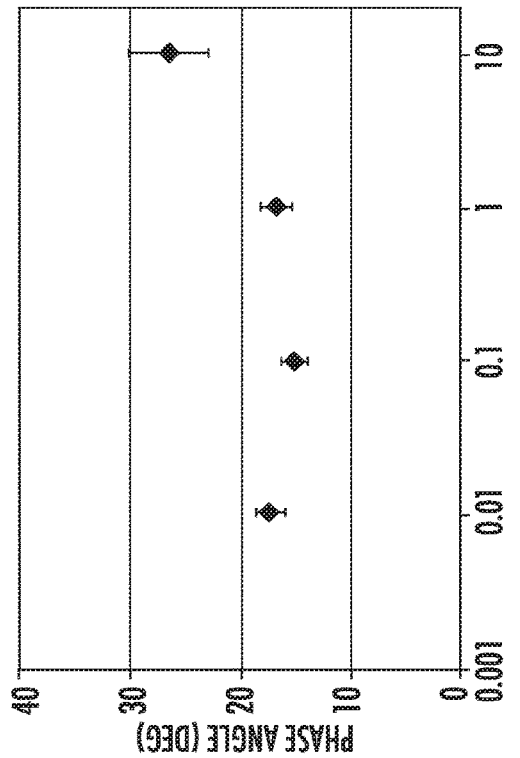
FIG. 8 provides graphical representation of dynamic mechanical analysis of treated tissue (panels A and B) compared to fresh tissue (panels C and D) tested to 8% compressive strain.
Figure 8B:
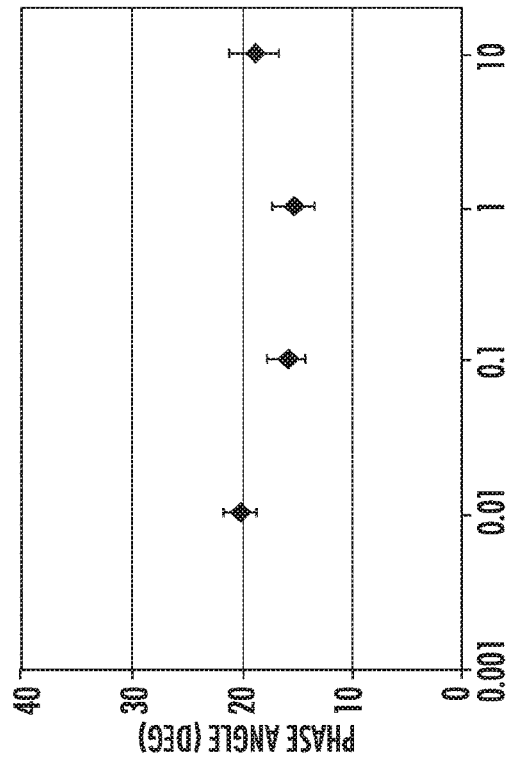
Figure 8C:
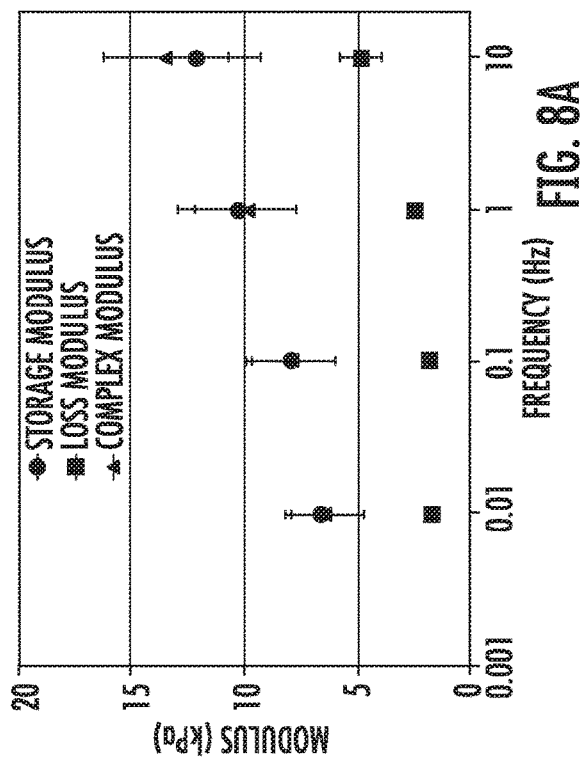
Figure 8D:
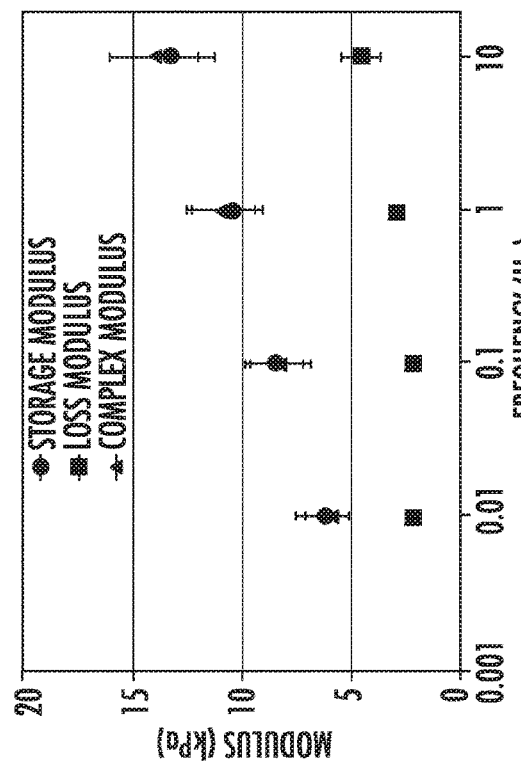

All mechanical testing results, with the exception of Poisson's ratio, were determined with respect to 8%, 12%, and 16% applied strain. Mean unconfined intrinsic equilibrium Young's modulus of ABNP scaffolds (10.13±1.58 kPa, 7.59±1.00 kPa, and 5.85±0.90 kPa) were significantly different at only the 8% strain increment ($p<0.05$) compared to fresh tissue scaffolds (42.18±13.36 kPa, 29.87±9.79 kPa, and 24.76±8.65 kPa) (FIG. 7, panel A). Percent relaxation of ABNP scaffolds (91.86±1.49%, 83.56±2.78%, and 84.67±2.74%) was not significantly different compared to fresh tissue (86.82±3.72%, 77.20±4.02%, and 77.75±4.10%) (FIG. 6, panel B and C, respectively). Apparent Poisson's ratio from 8-12% strain of ABNP scaffolds (0.142±0.026) was not significantly different compared to values obtained for fresh bovine NP (0.126±0.059). Shear modulus (FIG. 7, panel C) (4.44±0.69 kPa, 3.33±0.44 kPa, and 2.56±0.40 kPa) and aggregate modulus (FIG. 7, panel B) (10.62±1.66 kPa, 7.97±1.05 kPa, and 6.14±0.95 kPa) values for ABNP scaffolds were significantly different at only the 8% strain increment ($p<0.05$) compared to fresh tissue scaffolds (18.73±5.93 kPa, 13.26±4.35 kPa, and 11.00±3.84 kPa) and (43.77±13.86 kPa, 30.99±10.15 kPa, and 25.69±8.98 kPa), respectively.

Complex, storage, and loss moduli as well as the phase angle were evaluated across a range of frequencies using DMA (Table 2). No statistical differences were observed between the two groups at any of the frequencies tested. Moduli values for each study group demonstrated a test frequency dependent relationship. The range of values observed for ABNP scaffold for the complex, storage, and loss moduli (FIG. 8 panel A) and phase angle (FIG. 8 panel B) were 6.59-13.52 kPa, 6.35-12.11 kPa, 1.68-4.80 kPa, and 14.99-26.44°, respectively over the frequencies tested. Fresh tissue values were found within the ranges of 6.36-13.99 kPa, 5.99-13.13 kPa, 2.12-4.55 kPa (FIG. 8, panel C), and 15.36-20.16° (FIG. 8, panel D) respectively.

TABLE 2

| | Complex Modulus (kPa) | | | |
|---|---|---|---|---|
| Frequency (Hz) | 0.01 | 0.1 | 1 | 10 |
| ABNP | 6.59 ± 1.64 | 8.02 ± 1.96 | 9.96 ± 2.22 | 13.52 ± 2.82 |
| Fresh | 6.36 ± 1.13 | 8.56 ± 1.40 | 10.92 ± 1.59 | 13.99 ± 2.00 |
| Frequency | 0.01 | 0.1 | 1 | 10 |
| | Storage Modulus (kPa) | | | |
| ABNP | 6.35 ± 1.62 | 7.85 ± 1.92 | 10.25 ± 2.65 | 12.11 ± 2.85 |
| Fresh | 5.99 ± 1.11 | 8.23 ± 1.38 | 10.51 ± 156 | 13.13 ± 1.90 |
| | Loss Modulus (kPa) | | | |
| ABNP | 1.68 ± 0.29 | 1.83 ± 0.32 | 2.45 ± 0.41 | 4.80 ± 0.89 |
| Fresh | 2.12 ± 0.30 | 2.29 ± 0.39 | 2.86 ± 0.48 | 4.55 ± 0.83 |
| | Phase angle (°) | | | |
| ABNP | 17.3 ± 1.34 | 14.99 ± 1.17 | 16.66 ± 1.59 | 26.44 ± 3.53 |
| Fresh | 20.16 ± 1.61 | 15.93 ± 1.77 | 15.36 ± 1.96 | 18.9 ± 2.37 |

Figure 9:
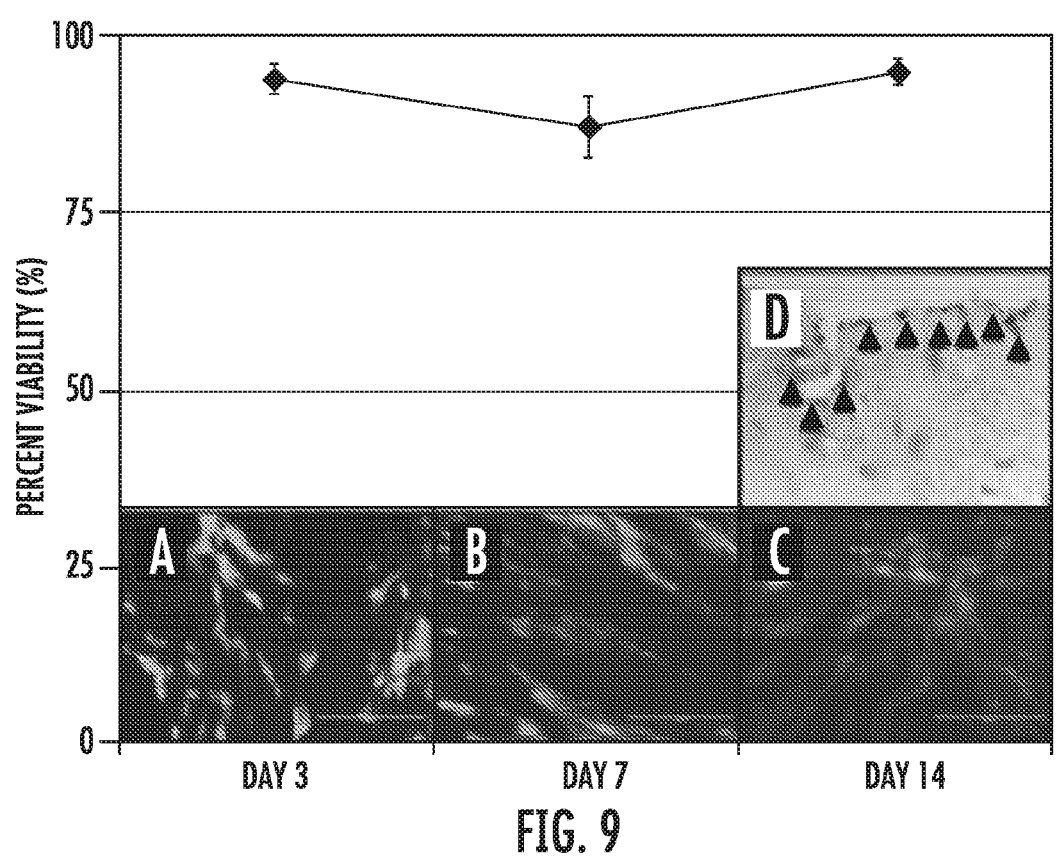
FIG. 9 presents live/dead staining on scaffolds seeded on the surface with hAMSCs for 3, 7, and 14 days (panels A, B, C, respectively). The graph provides the percent cell viability. Also shown are representative live dead images of hAMSC seeded scaffolds following 3 (A), 7 (B), and 14 (C) days of culture. Representative alcian blue stained scaffold seeded with hAMSCs (arrow heads) is shown at panel D following 14 days of culture. All images were obtained at 200× total magnification.

ABNP scaffold cytotoxicity was evaluated by seeding human amniotic mesenchymal stem cells (hAMSCs) onto the surface of ABNP scaffolds and culturing to 14 days. Live/dead fluorescence indicated cell viability to be 93.97±1.90%, 87.14±4.30%, and 95±1.46% at days 3, 7, and 14, respectively (FIG. 9, graph and panels A, B, C) indicating that the scaffold itself was not cytotoxic. There was no noticeable cell migration/penetration into the scaffolds throughout the duration of the study, as hAMSCs appeared to attach and spread on the surface of the scaffolds with increasing time in culture (FIG. 9, panel D).

Cell injection into non-crosslinked and EDC/NHS treated ABNP scaffolds was investigated since the hAMSCs did not infiltrate the scaffolds when seeded onto the surface. The stem cells were injected via a 28G syringe in order to minimize scaffold disruption due to needle stick. Viable cells were clearly visible within and around the injection path (FIG. 10, panels A-D). Viability of hAMSCs injected within non-crosslinked ABNP scaffolds were 91±4.99% and 97±1.44%, at day 3 and 14, respectively. Comparatively, viability on EDC/NHS crosslinked samples was 73±7.92% and 65±8.12%, respectively at day 3 and 14 (FIG. 10 panel E). In general, viability was maintained in both treatment groups over time in culture (i.e. there were no statistical significant differences in viability with respect to time within each study group); however, viability was significantly decreased (p<0.05) in the crosslinked scaffolds as compared to non-crosslinked ABNP at day 14. Of note, all injected hAMSCs maintained a round morphology reminiscent of NP-like cells within the scaffolds.

Example 2

Complete bovine caudal tail intervertebral discs were chosen as the source tissue material, as they have been shown to have similar size, biochemistry, and resting stress as compared to human lumbar intervertebral discs. Intact intervertebral discs were subjected to decellularization solutions and methods as described above and subsequently evaluated at defined regions around the disc for residual cell nuclei, DNA, and glycosaminoglycan (GAG) content via histology, picogreen and dimethylmethylene blue assays, respectively. Results were obtained from five intervertebral discs subjected to decellularization method no. 13 as described in Example 1. Results are expressed as an average±standard error of the mean (SEM). Significance was determined by comparing decellularized discs to fresh discs using paired t-tests with p<0.05 (*).

The macro- and microscopic architecture of the intervertebral discs remained intact following decellularization (FIG. 11), although swelling commonly occurred. Alcian blue staining confirmed the absence of residual bovine cell nuclei and DNA content in both the central nucleus pulposus and outer annulus fibrosis, which were reduced by 85% and 73.03%, respectively, as compared to fresh controls (Table 3). Qualitative fluorescence staining with ethidium (FIG. 12) demonstrated the absence of residual cell DNA in decellularized nucleus pulposus and annular fibrosus tissues within the intervertebral discs. GAG content in both the nucleus pulposus and annulus fibrosus regions of the decellularized intervertebral discs were significantly reduced when compared to fresh discs.

TABLE 3

| DNA/GAG | Tissue type | Decell/Fresh | Average ± SEM |
|---|---|---|---|
| DNA (ng/mg dry weight) | Nucleus pulposus | Decell | 47.12 ± 14.66 |
| | | Fresh | 314.28 ± 65.4 |
| | Annulus fibrosus | Decell | 65.99 ± 4.07 |
| | | Fresh | 244.67 ± 25.68 |
| GAG (ng/mg dry weight) | Nucleus pulposus | Decell | 258.21 ± 59.3 |
| | | Fresh | 677.20 ± 95.04 |
| | Annulus fibrosus | Decell | 132.71 ± 11.44 |
| | | Fresh | 252.70 ± 23.17 |

As shown, the method was successful in fully decellularizing intact intervertebral discs while maintaining its structure and extracellular matrix architecture. While there was a significant reduction in the amount of GAG in both the nucleus pulposus and annulus fibrosus regions of the decellularized discs, these quantities approached values found in the human intervertebral discs. Furthermore, it is expected that these values will increase upon seeding of human stem cells and their subsequent differentiation on the biomimetic scaffold.

While certain embodiments of the disclosed subject matter have been described using specific terms, such description is for illustrative purposes only, and it is to be understood that changes and variations may be made without departing from the spirit or scope of the subject matter.

What is claimed is:

1. A biomaterial comprising a decellularized bovine intervertebral disc tissue, the decellularized bovine intervertebral disc tissue being substantially free of cell nuclei of a source bovine intervertebral disc tissue, the decellularized bovine intervertebral disc tissue comprising decellularized nucleus pulposus tissue, the decellularized nucleus pulposus tissue having a glycosaminoglycan content of about 200 micrograms or greater per milligram dry weight of the decellularized nucleus pulposus tissue and having a nucleic acid content of about 50 nanograms or less per milligram dry weight of the decellularized nucleus pulposus tissue.

2. The biomaterial of claim 1, the decellularized intervertebral disc tissue having a ratio of glycosaminoglycan content to hydroxyproline content of from about 10:1 to about 25:1.

3. The biomaterial of claim 1, further comprising extrinsic cells.

4. The biomaterial of claim 3, wherein the extrinsic cells comprise stem cells.

5. The biomaterial of claim 1, wherein one or more components of the decellularized intervertebral disc tissue is crosslinked.

6. The biomaterial of claim 1, wherein the biomaterial is an implantable graft material.

7. The biomaterial of claim 6, wherein the implantable graft material is an implantable intervertebral disc graft.

8. The biomaterial of claim 1, wherein the biomaterial is an in vitro cellular scaffold material.

9. The biomaterial of claim 1, further comprising annulus fibrosus tissue.

10. The biomaterial of claim 1, wherein the biomaterial comprises an entire intervertebral disc.

* * * * *